US010806801B2

(12) United States Patent
Su et al.

(10) Patent No.: US 10,806,801 B2
(45) Date of Patent: Oct. 20, 2020

(54) PHARMACEUTICAL COMPOSITION AND METHODS FOR USING THE SAME

(71) Applicants: NATIONAL CHENG KUNG UNIVERSITY, Tainan (TW); NATIONAL CHENG KUNG UNIVERSITY HOSPITAL, Tainan (TW); NATIONAL TAIWAN NORMAL UNIVERSITY, Taipei (TW)

(72) Inventors: Wu-Chou Su, Tainan (TW); Hai-Wen Chen, Tainan (TW); Tsung-Lin Tsai, Tainan (TW); Dar-Bin Shieh, Tainan (TW); Chia-Chun Chen, Taipei (TW)

(73) Assignees: NATIONAL CHENG KUNG UNIVERSITY, Tainan (TW); NATIONAL CHENG KUNG UNIVERSITY HOSPITAL, Tainan (TW)

( * ) Notice: Subject to any disclaimer, the term of this patent is extended or adjusted under 35 U.S.C. 154(b) by 0 days.

(21) Appl. No.: 15/997,715

(22) Filed: Jun. 5, 2018

(65) Prior Publication Data
US 2018/0353612 A1 Dec. 13, 2018

Related U.S. Application Data

(60) Provisional application No. 62/516,494, filed on Jun. 7, 2017.

(51) Int. Cl.
| | |
|---|---|
| A61K 47/68 | (2017.01) |
| A61K 47/69 | (2017.01) |
| A61K 31/137 | (2006.01) |
| A61K 49/18 | (2006.01) |
| A61K 49/04 | (2006.01) |
| A61K 9/51 | (2006.01) |
| A61K 41/00 | (2020.01) |
| A61K 47/58 | (2017.01) |
| A61K 47/59 | (2017.01) |
| A61K 47/54 | (2017.01) |
| A61K 47/60 | (2017.01) |
| A61B 5/055 | (2006.01) |
| A61B 6/03 | (2006.01) |
| A61K 31/661 | (2006.01) |
| A61K 31/662 | (2006.01) |
| A61N 5/10 | (2006.01) |
| A61K 9/00 | (2006.01) |

(52) U.S. Cl.
CPC .......... *A61K 47/6929* (2017.08); *A61B 5/055* (2013.01); *A61B 6/032* (2013.01); *A61K 9/5115* (2013.01); *A61K 9/5138* (2013.01); *A61K 31/137* (2013.01); *A61K 31/661* (2013.01); *A61K 31/662* (2013.01); *A61K 41/0038* (2013.01); *A61K 47/542* (2017.08); *A61K 47/58* (2017.08); *A61K 47/593* (2017.08); *A61K 47/60* (2017.08); *A61K 47/6923* (2017.08); *A61K 47/6925* (2017.08); *A61K 49/04* (2013.01); *A61K 49/0428* (2013.01); *A61K 49/186* (2013.01); *A61K 49/1824* (2013.01); *A61K 49/1827* (2013.01); *A61K 49/1839* (2013.01); *A61K 49/1854* (2013.01); *A61N 5/10* (2013.01); *A61K 9/0009* (2013.01)

(58) Field of Classification Search
CPC ............ A61K 47/6929; A61K 47/6923; A61K 31/662
See application file for complete search history.

(56) References Cited

U.S. PATENT DOCUMENTS

| 7,807,217 B2 | 10/2010 | Shukla et al. | |
|---|---|---|---|
| 2011/0123439 A1* | 5/2011 | Cheon ................ | A61K 49/0002 424/1.37 |

(Continued)

FOREIGN PATENT DOCUMENTS

| CN | 102274519 A | 12/2011 |
|---|---|---|
| CN | 102436885 A | 5/2012 |

(Continued)

OTHER PUBLICATIONS

Tapan K Jain et al: "Iron oxide nanoparticles for sustained delivery of anticancer agents", Molecular Pharmaceutics, American Chemical Society, US, vol. 2, No. 3, Jun. 6, 2005 (Jun. 6, 2005), pp. 194-205, XP002672473, ISSN: 1543-8384, DOI: 10.1021/MP0500014.

(Continued)

*Primary Examiner* — Micah Paul Young
(74) *Attorney, Agent, or Firm* — ScienBiziP, P.C.

(57) ABSTRACT

A pharmaceutical composition includes a plurality of metal nanoparticles and at least one therapeutic agent. Each of the metal nanoparticles includes a core and a stabilizing agent coated on a surface of the core. The at least one therapeutic agent is attached to the stabilizing agent of the metal nanoparticles. Each of the therapeutic agent is an amphiphilic compound and has at least one hydrophobic chain interacting with the stabilizing agent. The pharmaceutical composition may further include a polymer shell encapsulating the metal nanoparticles and the therapeutic agent for enabling controlled release of the therapeutic agent. The pharmaceutical compositions are bifunctional and may be used for diagnosing and treating cancer. Methods for using the pharmaceutical compositions in conjunction with radiation therapy to diagnose and treat cancer are also provided.

25 Claims, 15 Drawing Sheets

(56) References Cited

U.S. PATENT DOCUMENTS

2013/0195767 A1* 8/2013 Weissleder ............ A61K 9/5094
424/9.323
2018/0311174 A1* 11/2018 Irvine ................ A61K 47/6923

FOREIGN PATENT DOCUMENTS

| CN | 104814930 A | 8/2015 |
| CN | 106334190 A | 1/2017 |
| CN | 106735287 A | 5/2017 |

OTHER PUBLICATIONS

Yanhui Jia et al: "Co-encapsulation of magnetic Fe3O4 nanoparticles and doxorubicin into biodegradable PLGA nanocarriers for intratumoral drug delivery", International Journal of Nanomedicine, Mar. 1, 2012 (Mar. 1, 2012), p. 1697, XP055491555, DOI: 10.2147/IJN.S28629.
Shun-Zhong Luo, "Nuclear technology application", Harbin Engineering University Press, Jan. 31, 2015 p. 195.

\* cited by examiner

PHARMACEUTICAL COMPOSITION AND METHODS FOR USING THE SAME

CROSS-REFERENCE TO RELATED APPLICATION

The present disclosure claims the benefit of U.S. Provisional Application No. 62/516,494, filed on Jun. 7, 2017, the entirety of which is incorporated herein by reference.

FIELD

The present disclosure generally relates to pharmaceutical compositions and methods for preparing and using the pharmaceutical compositions, and more particularly to nanoparticle-based pharmaceutical compositions that enhance the therapeutic effect of radiation therapies and can be used for diagnosing and treating cancers.

BACKGROUND OF THE DISCLOSURE

Taking advantage of the ability of nanoparticles to accumulate in tumor tissues, nanotechnology has been widely applied to clinical diagnosis or treatment of cancer. For example, nanoparticle-based computed tomography (CT) or magnetic resonance imaging (MRI) have been developed as diagnostic tools for tumors. Specifically, nanoparticles that have been reported to be used for CR or MRI include iron oxide, nano-gold, quantum dots and FePt, and constituent alloys of.

In existing clinical applications of nanoparticles, a patient needs to be injected or administered with contrast agents (such as iodine) before CT or MRI imaging, from which the clinician determines whether the patient is suffering from cancer, what type of cancer it is, and how to treat the cancer. In cancer treatments that require a surgery, the surgery is typically combined with chemotherapy and radiation therapies to enhance the therapeutic effect of the treatments.

However, asynchronism between diagnosis and treatment has led to long period of cancer treatments that could last for 5 to 10 years. In addition, a single contrast agent can only be used on a single developing instrument during the diagnostic process. That is, if different instruments are used to diagnosis a patient, different contrast agents would be required to be introduced into the patient's body. Thereby, the diagnostic and treatment processes have been asynchronous, causing inconvenience and inaccuracy. Moreover, in follow-up treatments, the implementation of chemotherapy or radiation therapy is not synchronized with imaging diagnosis, and drug release is not simultaneously controlled. Thereby, treatment of a tumor site often results in discomfort and adverse side effects.

Features and advantages of the subject matter hereof will become more apparent in light of the following detailed descriptions of exemplary embodiments, as illustrated in the accompanying figures. As will be realized, the subject matter disclosed and claimed herein is capable of modifications in various respects, all without departing from the scope of the claims. Accordingly, the drawings and the description are to be regarded as illustrative in nature, and not as restrictive in relation to the full scope of the subject matter as set forth in the claims.

BRIEF SUMMARY OF THE DISCLOSURE

An objective of the present disclosure is to provide a bifunctional pharmaceutical composition that can diagnose and treat cancer synchronously.

Another objective of the present disclosure is to provide a pharmaceutical composition that enhances therapeutic effect of radiation therapies and sensitizes cancer cells to cancer treatments.

According to an embodiment of the present disclosure, a pharmaceutical composition includes a plurality of metal nanoparticles and at least one therapeutic agent. Each of the metal nanoparticles includes a core and a stabilizing agent coated on a surface of the core. The at least one therapeutic agent is attached to the stabilizing agent of the metal nanoparticle. Each of the therapeutic agent is an amphiphilic compound and has at least one hydrophobic chain interacting with the stabilizing agent.

Preferably, the metal nanoparticles are iron-platinum (FePt) nanoparticles.

Preferably, the average diameter of the FePt nanoparticles falls substantially within a range of 3 nanometers (nm) to 13 nm.

Preferably, the stabilizing agent is oleic acid.

Preferably, the at least one therapeutic agent is an anti-cancer drug, an anti-inflammatory agent, or a combination thereof.

Preferably, the at least one therapeutic agent is 2-amino-2-[2-(4-octylphenyl)ethyl]-1,3-propanediol (FTY720), derivatives of FTY720, 2-amino-N-(3-octylphenyl)-3-(phosphonooxy)-propanamaide (VPC 23019), derivatives of VPC 23019. [(3R)-3-amino-4-[(3-hexylphenyl)amino]-4-oxobutyl]-phosphonic acid (W146), derivatives of W146 or any combination thereof.

Preferably, the mass ratio of the metal nanoparticles to the at least one therapeutic agent falls substantially within a range of 1:0.01 to 1:100.

Preferably, the pharmaceutical composition further includes a polymer shell encapsulating the metal nanoparticles and the therapeutic agent.

Preferably, the polymer shell enables controlled release of the therapeutic agent.

Preferably, the polymer shell includes polyvinyl alcohol (PVA), poly (lactic-co-glycolic acid) (PLGA), polyethylene glycol (PEG), D-α-tocopherol polyethylene glycol 1000 succinate (TPGS), or any combination thereof.

Preferably, the weight percentage of the polymer shell in the pharmaceutical composition falls within a range of 0.1% to 10%.

Preferably, the pharmaceutical composition further includes an adaptor agent linking the therapeutic agent to the stabilizing agent of the metal nanoparticles.

Preferably, the pharmaceutical composition is bifunctional and used for diagnosing and treating cancer.

Preferably, the cancer diagnosed and treated by the pharmaceutical composition includes lung carcinoma or breast cancer.

According to another embodiment of the present disclosure, a method for using the pharmaceutical composition includes a step of: administering a therapeutically effective amount of the pharmaceutical composition to a subject.

Preferably, the method further includes a step of: administering an effective amount of radiation energy to the subject. The effective amount of radiation energy is sufficient to treat cancer in the subject.

Preferably, the method further includes a step of: subjecting the subject to magnetic resonance imaging or computed tomography scanning to diagnose cancer in the subject.

Preferably, the method further includes the steps of: subjecting the subject to magnetic resonance imaging or computed tomography scanning to diagnose cancer in the subject; and administering an effective amount of radiation energy to the subject.

Preferably, the method further includes a step of: providing an effective amount of radiation energy to the pharmaceutical composition to release the therapeutic agent into the subject.

Preferably, the method further includes the steps of: subjecting the subject to magnetic resonance imaging or computed tomography scanning to diagnose cancer in the subject; and providing an effective amount of radiation energy to the pharmaceutical composition to release the therapeutic agent into the subject.

In sum, according to various embodiments of the present disclosure, the pharmaceutical compositions allow simultaneous use for diagnosis and treatment of cancer. The therapeutic agent carried by the metal nanoparticles in the pharmaceutical compositions can accumulate in tumor tissues, therefore enabling the pharmaceutical compositions to act as contrast agents for CT/MRI dual scanning, enhancers for enhancing therapeutic effect of radiation therapy by generating free radicals to destroy cancerous cells, and/or sensitizers for enhancing sensibility of cancerous cells to radiation or chemotherapies. The polymer shell of the pharmaceutical compositions also allows controlled release the therapeutic agent to the tumor tissues, therefore avoiding adverse side effects caused by non-specific release of the therapeutic agent to normal tissues.

BRIEF DESCRIPTION OF THE DRAWINGS

Implementations of the present disclosure will now be described, by way of examples only, with reference to the accompanying figures.

DETAILED DESCRIPTION OF THE PREFERRED EMBODIMENTS

Figure 1A:
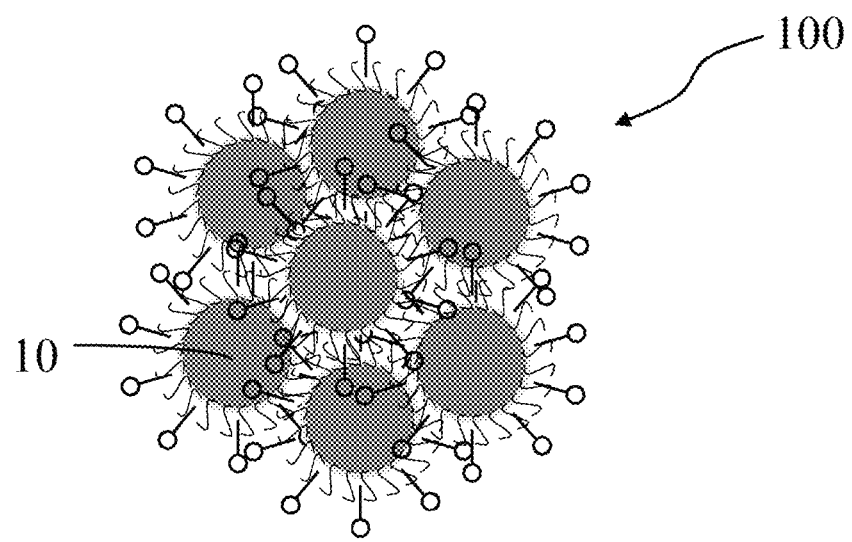
FIG. 1A is a schematic illustration of a pharmaceutical composition having a plurality of metal nanocomposites in accordance with a first embodiment of the present disclosure.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. The drawings are not necessarily to scale and the proportions of certain parts may be exaggerated to better illustrate details and features. The description is not to be considered as limiting the scope of the embodiments described herein.

Several definitions that apply throughout this disclosure will now be presented.

The term "substantially" means essentially conforming to the particular dimension, shape or other feature that the term modifies, such that the component need not be exact. The term "comprising" or "containing" when utilized, means "including, but not necessarily limited to"; it specifically indicates open-ended inclusion or membership in the so-described combination, group, series, and the like. The term "applying" is the act of bringing things into contact or of starting an action. The term "administering" means dispensing or providing something to a subject, such as dispensing a drug composition, or providing a radiation.

As used herein, the terms "subject" and "patient" are used interchangeably and refer to a mammal, usually a human.

As used herein, the term "therapeutically effective amount" means a dose that is sufficient to achieve a desired therapeutic effect for which it is administered. The exact dose will be ascertainable by one skilled in the art using known techniques, and efficacy can be measured in conventional ways. For cancer therapy, efficacy of a therapeutic effect can, for example, be measured by assessing the time for regression or progression, determining response rates, time to relapse, tumor size, etc. The term "effective amount" means a dose that is sufficient to achieve a desired effect for which it is administered. The administered object can be a composition, a drug, a dose of energy, or a therapy. The desired effect, for example, can be a diagnostic effect, an imaging effect, a therapeutic effect, or an effect of agent releasing.

The term "pharmaceutically acceptable" as used herein means approved by a regulatory agency of the Federal or a state government or listed in the U.S. Pharmacopeia or other generally recognized pharmacopeia for use in animals, and more particularly, in humans.

The present disclosure is described in relation to a pharmaceutical composition, and methods for preparing and using the pharmaceutical composition.

According to an embodiment of the present disclosure, a pharmaceutical composition for diagnosing and treating cancer includes a plurality of metal nanoparticles and at least one therapeutic agent. Each of the metal nanoparticles includes a core and a stabilizing agent coated on the surface of the core. The stabilizing agent is used for increasing stability of the metal nanoparticles. Each therapeutic agent may be an amphiphilic compound, and has at least one hydrophobic chain interacting with the stabilizing agent. In at least one embodiment, the pharmaceutical composition is bifunctional and may be used for diagnosing and treating cancer. The pharmaceutical composition may further include an adaptor agent for linking the therapeutic agent to the stabilizing agent of the metal nanoparticles.

According to an embodiment of the present disclosure, another pharmaceutical composition for diagnosing and treating a cancer includes a plurality of metal nanoparticles, at least one therapeutic agent, and at least one polymer shell. Each metal nanoparticle includes a core and a stabilizing agent coating on the surface of the core. The stabilizing agent increases the stability of the metal nanoparticle. The polymer shell encapsulates the metal nanoparticle and the therapeutic agent. In the embodiment, each of the therapeutic agent is an amphiphilic compound, and has at least one hydrophobic chain interacting with the stabilizing agent. The polymer shell enables controlled release and prevents non-specific release of the therapeutic agent. In the embodiment, the pharmaceutical composition is bifunctional and may be used for diagnosing and treating cancer. The pharmaceutical composition may further include the adaptor agent for linking the therapeutic agent with the stabilizing agent of the metal nanoparticles.

According to an embodiment of the present disclosure, a method for preparing the pharmaceutical composition includes the steps of: dissolving a plurality of metal nanoparticles in an organic solvent to obtain a metal nanoparticles solution; mixing the metal nanoparticles solution with an amphiphilic therapeutic agent to obtain a mixture; and removing the organic solvent from the mixture to obtain the pharmaceutical composition.

In an embodiment, the method for preparing the pharmaceutical composition may further include a step of: adding an adaptor agent before mixing the metal nanoparticles solution with the therapeutic agent, to facilitate linking the therapeutic agent to the metal nanoparticles.

According to an embodiment of the present disclosure, another method for preparing the pharmaceutical composition includes the steps of: dissolving a plurality of metal nanoparticles in an organic solvent to obtain a metal nanoparticle solution; mixing the metal nanoparticles solution with an amphiphilic therapeutic agent to obtain a mixture; adding a polymer to the mixture; and removing the organic solvent from the mixture to obtain the pharmaceutical composition.

In an embodiment, the method for preparing the pharmaceutical composition may further include a step of: adding an adaptor agent before mixing the metal nanoparticles solution with the therapeutic agent, to facilitate linking the therapeutic agent to the metal nanoparticles.

Referring to FIG. 1A. According to a first embodiment of the present disclosure, a pharmaceutical composition 100 includes a plurality of metal nanocomposites 10 and a pharmaceutically acceptable carrier (not shown). In the embodiment, the diameter of each of the metal nanocomposites 10 of the pharmaceutical composition 100 may fall substantially within a range of 10 nm to 1000 nm, or preferably 10 nm to 200 nm or other size range that results in higher bio-absorbability and safety of nanoparticle based pharmaceutical composition. The pharmaceutical composition 100 may be given to a subject orally, intravenously, subcutaneously, or intramuscularly.

Figure 1B:
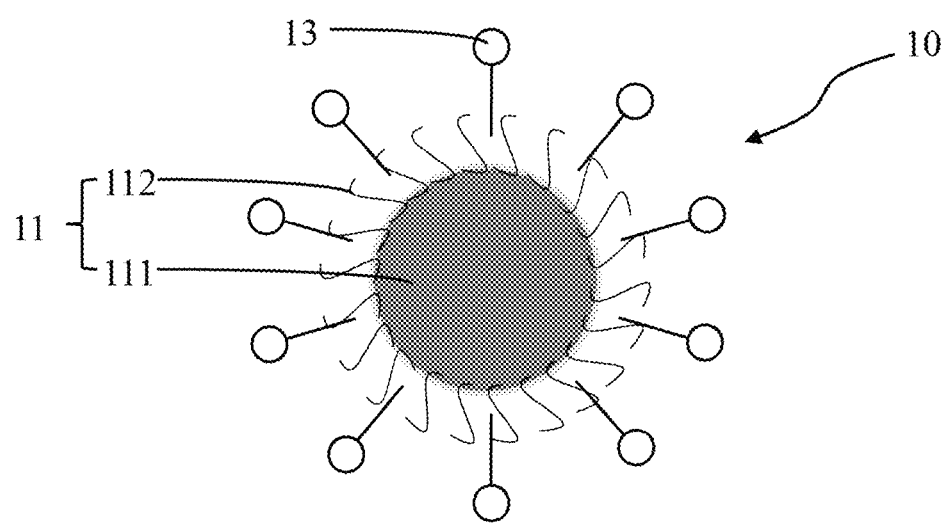
FIG. 1B is a schematic illustration of one of the metal composites in accordance with the first embodiment of the present disclosure.

Referring to FIG. 1B. In the first embodiment, each of the metal nanocomposites 10 includes a metal nanoparticle 11 and at least one therapeutic agent 13 formed on a surface of the metal nanoparticle 11. The metal nanoparticle 11 includes a core 111 and a stabilizing agent 112 coated on a surface of the core 111. The stabilizing agent 112 is adopted to increase the stability of the metal nanoparticle 11. The at least one therapeutic agent 13 is attached to the stabilizing agent 112 of the metal nanoparticle 11.

In the first embodiment, a mass ratio of the metal nanoparticle 11 to the therapeutic agent 13 may fall substantially within the range of 1:0.01 to 1:100. The core 111 of the metal nanoparticle 11 may be made of metal, alloy, metal oxide, metalloid, metalloid oxide, magnetic nanoparticles, or any combination thereof. The metal may include, but is not limited to, gold, silver, copper, titanium, nickel, platinum, palladium, metal of the lanthanide series or any combination thereof. The metal oxide may include, but is not limited to, $TiO_2$. The magnetic nanoparticles may include, but are not limited to, iron nanoparticles, iron composite nanoparticles, or a combination thereof; and the iron composite nanoparticles may include, but are not limited to, $Fe_2O_3$, $Fe_3O_4$, FePt, FeCo, FeAl, FeCoAl, $CoFe_2O_4$, $MnFeO_4$, CoPt, or any combination thereof.

Preferably, the metal nanoparticle 11 are FePt nanoparticles (hereinafter FePt NPs). A lattice structure of the FePt NPs may be a face-centered cubic (fcc) structure. An average diameter of each of the FePt NPs may fall substantially within a range of 3 nm to 13 nm, or preferably 6 nm to 7 nm. A general formula of the FePt NPs may be $Fe_{58}Pt_{42}$.

FePt NPs can be used to diagnose and treat cancer, especially malignant tumors. For example, FePt NPs may be utilized as contrast agents for both of computed tomography (CT) and magnetic resonance imaging (MRI); that is. FePt NPs possess suitable characteristics for CT/MRI dual imaging. FePt NPs can also accumulate in tumor tissues of a living subject and absorb radiation energy, therefore allowing radiation to focus on and effectively kill the tumor tissues in vivo. In other embodiments, FePt NPs can be adopted as a drug carrier, for example, for delivering cancer treating drugs. Consequently, tumor tissues may be treated by radiation and drugs delivered by FePt NPs simultaneously, thereby enhancing the synergistic effect of chemotherapy and radiotherapy. FePt NPs may also function as a radiation therapy enhancer, as FePt NPs, when absorbing radiation, can be activated to split water molecules surrounding the FePt NPs, thus generating free radicals that destroy cancerous cells.

The stabilizing agent 112 stabilizes the core 111 of the metal nanoparticle 11 and maintains a uniformed size distribution of the metal nanoparticles 11, and may be a surfactant, for example cationic surfactant, neutral surfactant, or anionic surfactant. The cationic surfactant may include, but is not limited to, alkyl trimethylammonium halide. The neutral surfactant may include, but is not limited to, saturated fatty acid or unsaturated fatty acid, such as oleic acid, lauric acid, dodecylic acid, trialkylphosphine, a trialkylphosphine oxide (e.g., trioctylphosphine oxide (TOPO), trioctylphosphine (TOP), or tributylphosphine), alkyl amine (e.g., dodecylamine, oleicamine, trioctylamine, or octylamine), or alkyl thiol. Specifically, oleic acids increase hydrophobicity of the metal nanoparticles, therefore stabilizing the core 111 of the metal nanoparticle 11. The anionic surfactant may include, but is not limited to, sodium alkyl phosphate.

The at least one therapeutic agent 13 may be an amphiphilic compound, and has at least one hydrophobic chain interacting with the stabilizing agent 112. The therapeutic agent 13 may include, but is not limited to, an anti-metabolitic agent, anti-fungal agent, anti-infective agent, antibiotic agent, nutritive compound, agonistic compound, antagonistic compound, or preferably an anti-cancer drug, an anti-tumoral agent, an anti-inflammatory agent, or any combination thereof. Specifically, the therapeutic agent 13 may be 2-amino-2-[2-(4-octylphenyl)ethyl]-1,3-propanediol (FTY720), derivatives of FTY720, 2-amino-N-(3-octylphenyl)-3-(phosphonooxy)-propanamaide (VPC 23019), derivatives of VPC 23019, [(3R)-3-amino-4-[(3-hexylphenyl)amino]-4-oxobutyl]-phosphonic acid (W146), derivatives of W146 or any combination thereof.

More specifically, the therapeutic agent 13 is most preferably FTY720, for that FTY720 can act a radiation therapy sensitizer that enhances vulnerability of treated tumor cells to radiation. In an embodiment in which FTY720 is adopted as the therapeutic agent 13, FTY720 is attached to the surface of each of the FePt NPs, forming a pharmaceutical composition hereinafter referred to as FePt@FTY720 NPs. In the embodiment, the mass ratio of the FePt NPs to FTY720 is in the range of 1:0.01 to 1:100.

Figure 2A:
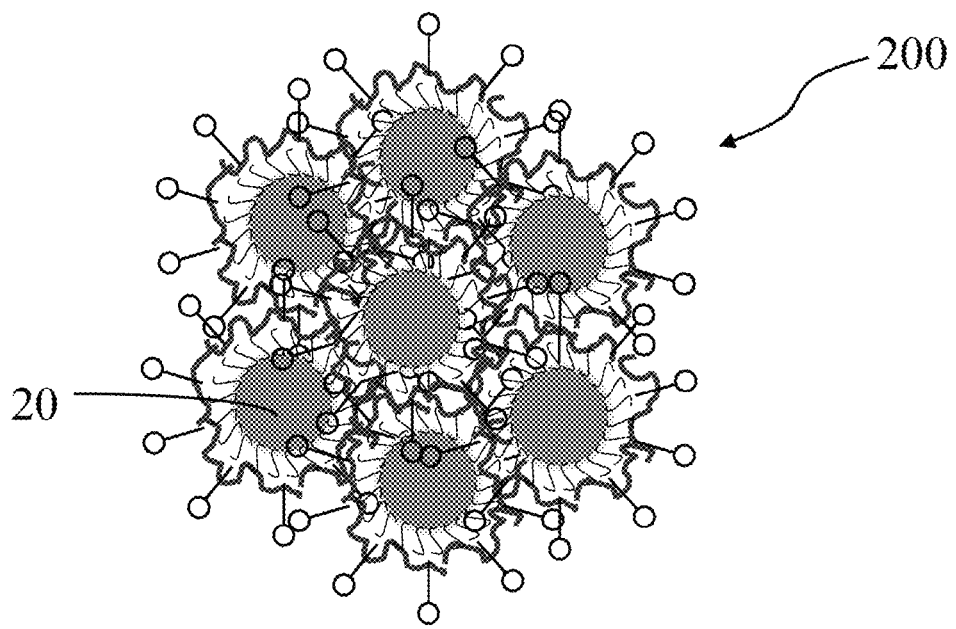
FIG. 2A is a schematic illustration of a pharmaceutical composition having a plurality of metal nanocomposites in accordance with a second embodiment of the present disclosure.

Referring to FIG. 2A. According to a second embodiment of the present disclosure, a pharmaceutical composition 200 includes a plurality of metal nanocomposites 20 and a pharmaceutically acceptable carrier (not shown). A diameter of the metal nanocomposites 20 in the pharmaceutical composition 200 may fall substantially within a range of 10 nm to 1000 nm, or preferably 10 nm to 200 nm or other size range that results in higher bio-absorbability and safety of the pharmaceutical composition.

Figure 2B:
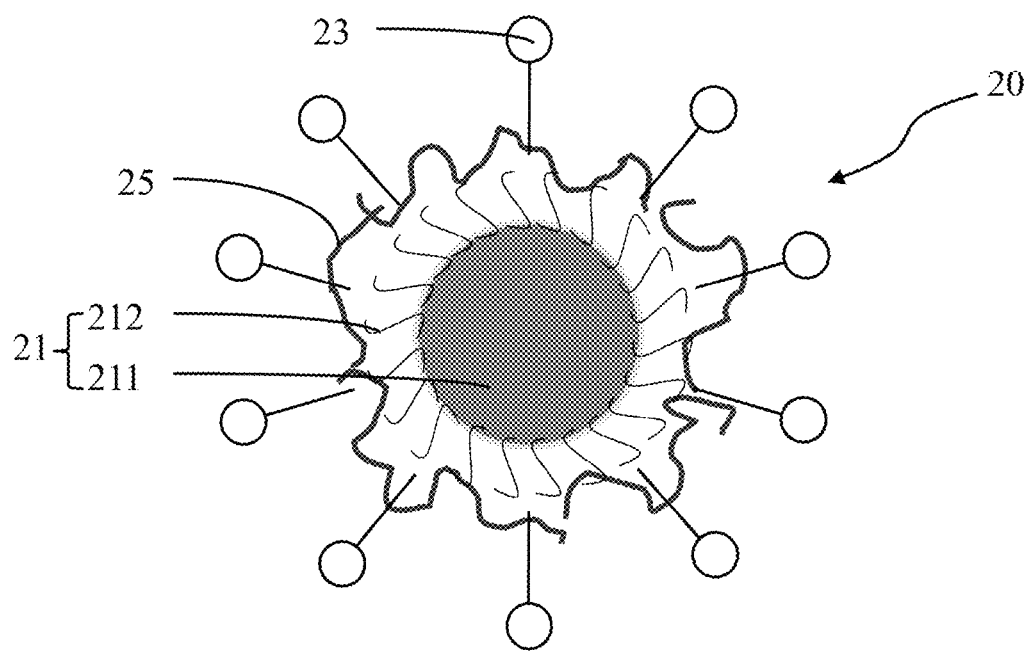
FIG. 2B is a schematic illustration of one of the metal nanocomposite in accordance with the second embodiment of the present disclosure.

Referring to FIG. 2B. In the second embodiment, each of the metal nanocomposites 20 includes a metal nanoparticle 21 and at least one therapeutic agent 23. The metal nanoparticle 21 includes a core 211 and a stabilizing agent 212 coated on a surface of the core 211. The stabilizing agent 212 increases stability of the metal nanoparticles 21. Features and properties of the nanoparticle 21 and the at least one therapeutic agent 23 are substantially identical to those of the first embodiment. The difference between the two embodiments lies in that the metal nanocomposite 20 of the second embodiment further includes an adaptor agent 25 for linking the stabilizing agent 212 to the therapeutic agents 23.

The adaptor agent 25 may be, but is not limited to, a polymer, such as cellulose, polyethyleneglycol (PEG), poly (N-vinyl pyrrolidone), poly(alkylcyanoacrylate), poly-ε-caprolactone, derivatives thereof, or any combination thereof.

In the second embodiment, the therapeutic agent 23 forms on a surface of each of the metal nanoparticles 21, and the adaptor agent 25 links the metal nanoparticles 21 to the therapeutic agents 23. A mass ratio of the metal nanoparticles 21 to the therapeutic agent 23 may fall substantially within the range of 1:0.01 to 1:100. In a preferred embodiment, the metal nanoparticles 21 is FePt NPs, the therapeutic agent 23 is FTY720, and the adaptor agent 25 is PEG, thereby forming hydrophilic FePt@PEG NPs a pharmaceutical composition hereinafter referred to as FePt@PEG-FTY720 NPs.

Figure 3:
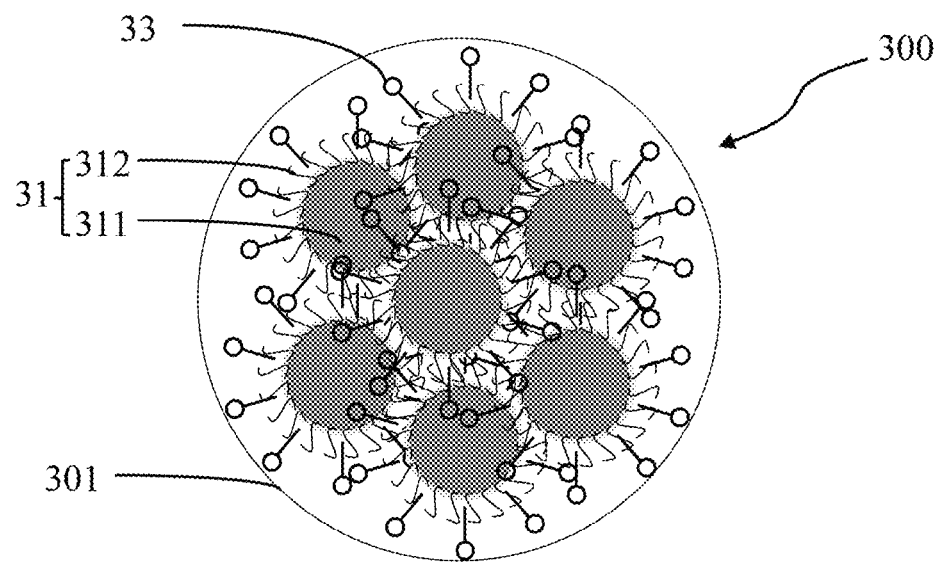
FIG. 3 is a schematic illustration of a pharmaceutical composition in accordance with a third embodiment of the present disclosure.

Referring to FIG. 3. In a third embodiment of the present disclosure, a pharmaceutical composition 300 includes a plurality of metal nanoparticles 31 and at least one therapeutic agent 33. Each of the metal nanoparticles 31 includes a core 311 and a stabilizing agent 312 coated on a surface of the core 311. The stabilizing agent 312 increases the stability of the metal nanoparticles 31. Features and properties of the metal nanoparticles 31 and the at least one therapeutic agent 33 are substantially identical to those of the first embodiment. The difference between the two embodiments lies in that the pharmaceutical composition 300 of the third embodiment further includes a polymer shell 301 encapsulating the metal nanoparticles 31 and the at least one therapeutic agent 33.

In the embodiment, the polymer shell 301 may, but is not limited to, be made of a biodegradable polymer, such as polyvinyl alcohol (PVA), poly (lactic-co-glycolic acid) (PLGA), polyethylene glycol (PEG), D-β-tocopherol polyethylene glycol 1000 succinate (TPGS), or any combination thereof. Preferably, the polymer shell 301 is made of polyvinyl alcohol. A weight percentage of the polymer shell 301 in the pharmaceutical composition 300 falls substantially within a range of 0.1% to 10%, or preferably 0.25% to 5%.

The polymer shell 301 enables controlled release of the at least one therapeutic agent 33 at a targeted tumor site and prevents the therapeutic agent 33 from non-specific release at non-targeted sites, therefore avoiding the side effects caused by release of the therapeutic agent 33 into normal non-cancerous tissues.

A diameter of the nanoparticles of the pharmaceutical composition 300 may fall substantially within a range of 10 nm to 1000 nm, or preferably 10 nm to 200 nm or other size range that results in higher bio-absorbability and safety of the pharmaceutical composition.

In a preferred embodiment, the metal nanoparticles 31 are FePt NPs, the therapeutic agent 33 is FTY720, and the polymer is polyvinyl alcohol (PVA), thereby forming FePt@FTY720 NPs and a pharmaceutical composition hereinafter referred to as FePt@FTY720-PVA NPs. A mass ratio of the FePt NPs to FTY720 falls within the range of 1:0.01 to 1:100. A weight percentage of PVA in the pharmaceutical composition 300 may fall substantially within a range of 0.1% to 10%, or preferably 0.25% and about 5% of the total.

Figure 4:
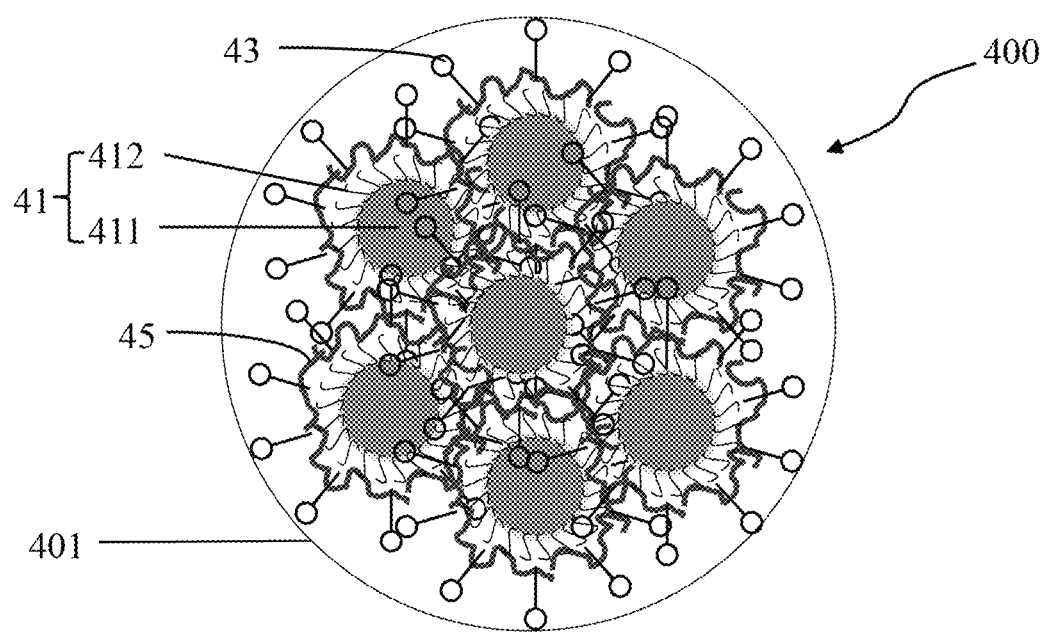
FIG. 4 is a schematic illustration of a pharmaceutical composition in accordance with a fourth embodiment of the present disclosure.

Referring to FIG. 4. In a fourth embodiment of the present disclosure, a pharmaceutical composition 400 includes a plurality of metal nanoparticles 41 and at least one therapeutic agent 43. Each of the metal nanoparticles 41 includes a core 411 and a stabilizing agent 412 coated on a surface of the core 411. The stabilizing agent 412 increases the stability of the metal nanoparticles 41. Features and properties of the nanoparticle 41 and the at least one therapeutic agent 43 are substantially identical to those of the second embodiment. The difference between the two embodiments lie in that the pharmaceutical composition 400 of the fourth embodiment further includes a polymer shell 401 encapsulating the nanoparticles 41 and the at least one therapeutic agent 43.

The polymer shell 401 of the fourth embodiment is substantially identical to the polymer shell 301 of the third embodiment. In the embodiment, the polymer shell 401 is preferably made of polyvinyl alcohol. A weight percentage of the polyvinyl alcohol in the pharmaceutical composition 400 may fall substantially within a range of 0.1% to 10%, or preferably 0.25% to 5%.

A diameter of the nanoparticles of the pharmaceutical composition 400 may fall substantially within a range of 10 nm to 1000 nm, or preferably 10 nm to 200 nm, or other size range that results in higher bio-absorbability and safety of the pharmaceutical composition.

Figure 5:
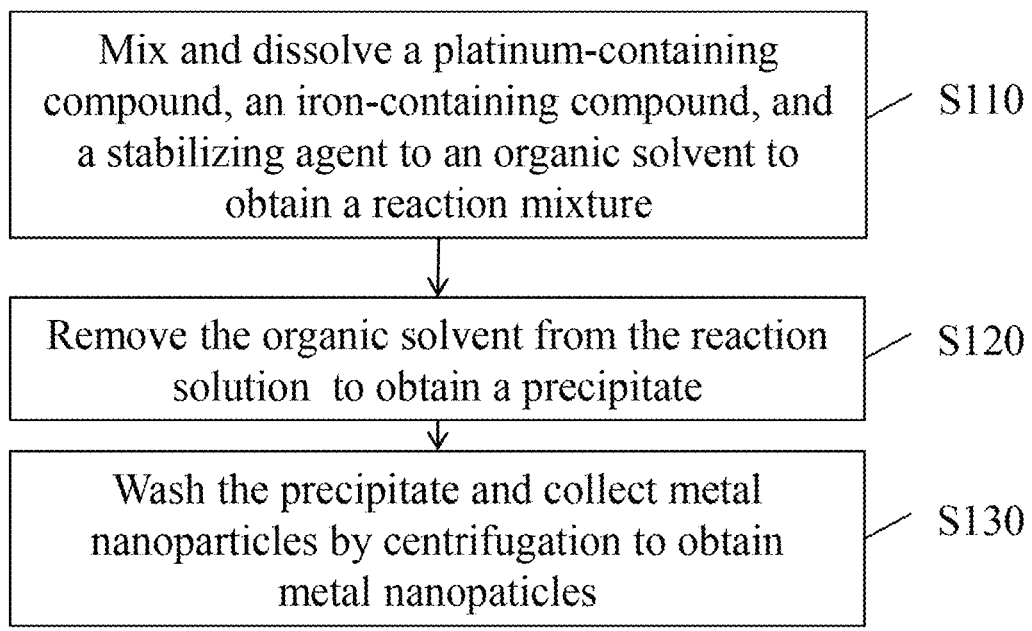
FIG. 5 is a flow diagram of a method for preparing metal nanoparticles in accordance with an embodiment of the present disclosure.

Referring to FIG. 5. According to an embodiment of the present disclosure, a method for preparing FePt NPs includes the steps of: (S110) mixing and dissolving a platinum-containing compound, an iron-containing compound, and a stabilizing agent to an organic solvent to obtain a reaction mixture; (S120) removing the organic solvent from the reaction mixture to obtain a precipitate; and (S130) washing the precipitate and collecting the precipitate by centrifugation metal nanoparticles.

In a preferred embodiment, the iron-containing compound is $Fe(CO)_5$, the stabilizing agent is oleic acid, the organic solvent is dioctyl ether, 1,2-hexadecandiol and oleylamine, and the platinum-containing compound is $Pt(acac)_2$. The resulting metal nanoparticles FePt NPs are covered with oleic acid.

In an example, the method for preparing FePt NPs having a particle diameter of 3-4 nm includes the steps of: mixing 97 mg of $Pt(acac)_2$, 195 mg of 1,2-hexadecandiol, and 10 mL of dioctyl ether to obtain a mixture; heating the mixture to 100° C. under $N_2$ for 10 min; injecting 66 μL of $Fe(CO)_5$, 80 μL of oleylamine, and 80 μL of oleic acid to the mixture at 100° C.; heating the mixture to 297° C. at heating rate of 15° C./min; heating the reaction mixture at 297° C. for 30 min; and cooling the mixture to room temperature to obtain a plurality of particles; washing the particles by hexane/alcohol for three times; and collecting the particles by centrifugation to obtain FePt NPs having a particle diameter of 3 nm-4 nm.

In another example, the method for preparing FePt NPs having a particle diameter of 6-7 nm by chemical reduction includes the steps of: mixing 97 mg of $Pt(acac)_2$, 4 mL of dioctyl ether, 66 uL of $Fe(CO)_5$, 195 mg of 1,2-hexadecandiol, 100 uL of oleylamine, and 100 uL of oleic acid under nitrogen to obtain a reaction mixture; heating the reaction mixture to 240° C. at heating rate of 15° C./min; heating the reaction mixture at 240° C. for 30 minutes; cooling the reaction mixture to room temperature to obtain a plurality of particles; washing the particles by hexane/alcohol for three times; and collecting the particles by centrifugation to obtain FePt NPs having a particle diameter of 6 nm-7 nm.

In yet another example, the method for preparing FePt NPs having a particle diameter of 12 nm-13 nm includes the steps of: mixing 195 mg of $Pt(acac)_2$, 1.05 g of 1,2-hexadecandiol, 4 mL of dioctyl ether, 66 μL $Fe(CO)_5$, 4 mL of oleylamine, and 4 mL of oleic acid under $N_2$ to obtain a reaction mixture; heating the reaction mixture to 240° C. at heating rate of 15° C./min; heating the reaction mixture at 240° C. for 60 min; cooling the reaction mixture to room temperature to obtain a plurality of particles; washing the particles by hexane/alcohol for three times; and collecting the particles by centrifugation to obtain FePt NPs having a particle diameter of 12 nm-13 nm.

Figure 6:
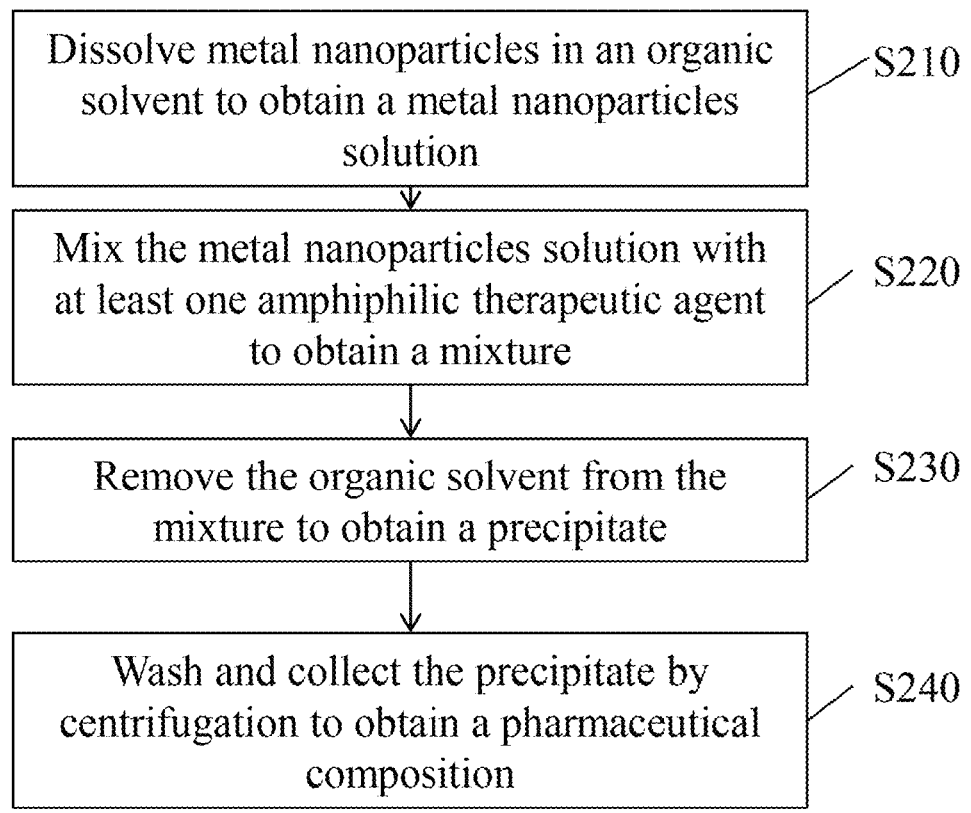
FIG. 6 is a flow diagram of the method for preparing FePt@FTY720 nanoparticles (NPs) in accordance with an embodiment of the present disclosure.

Referring to FIG. 6. According to an embodiment of the present disclosure, the method for preparing a pharmaceutical composition containing metal nanoparticles covered with a therapeutic agent includes the steps of: (S210) dissolving metal nanoparticles in an organic solvent to obtain a metal nanoparticles solution; (S220) mixing the metal nanoparticles solution with at least one amphiphilic therapeutic agent to obtain a mixture; (S230) removing the organic solvent from the mixture to obtain a precipitate; and (S240) washing and collecting the precipitate by centrifugation to obtain the pharmaceutical composition.

Figure 7:
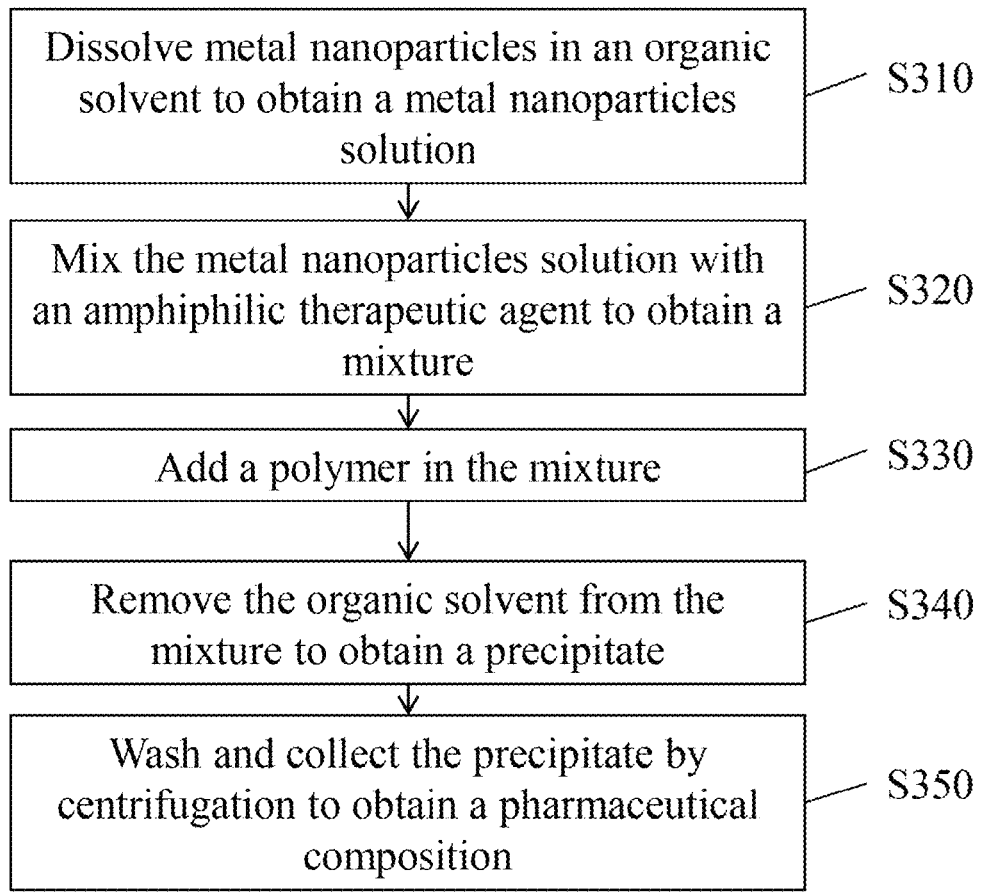
FIG. 7 is a flow diagram of the method for preparing FePt@FTY720-PVA NPs in accordance with an embodiment of the present disclosure.

Referring to FIG. 7. According to an embodiment of the present disclosure, the method for preparing a pharmaceutical composition containing metal nanoparticles covered with a therapeutic agent and encapsulated by a polymer shell includes the steps of: (S310) dissolving metal nanoparticles in an organic solvent to obtain a metal nanoparticles solution; (S320) mixing the metal nanoparticles solution with an amphiphilic therapeutic agent to obtain a mixture; (S330) adding a polymer in the mixture; and (S340) removing organic solvent from the mixture to obtain a precipitate; and (S350) washing and collecting the precipitate by centrifugation to obtain the pharmaceutical composition.

Figure 8:
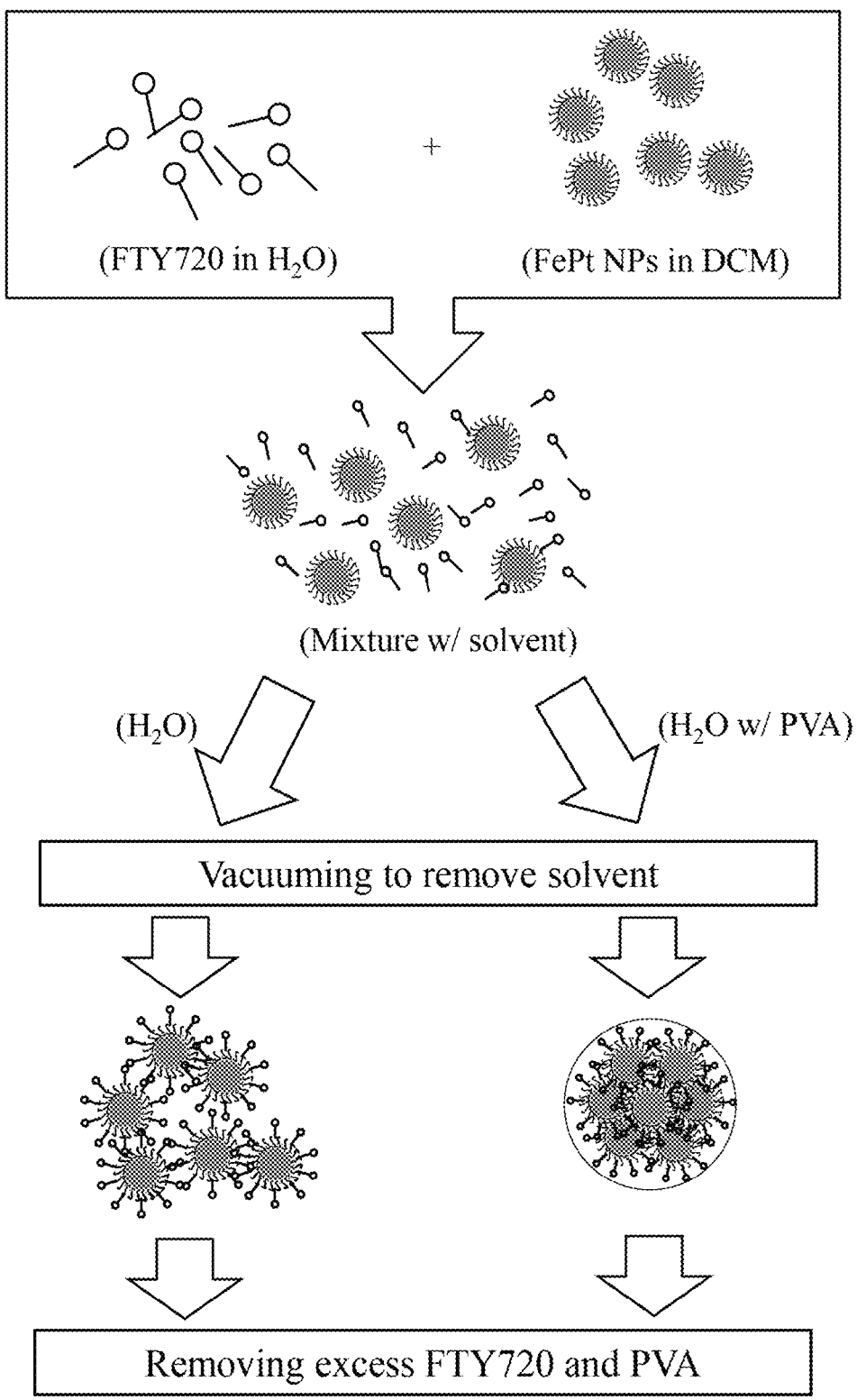
FIG. 8 is a schematic illustration of the steps of preparing the pharmaceutical compositions in accordance with an embodiment of the present disclosure.
Figure 9A:
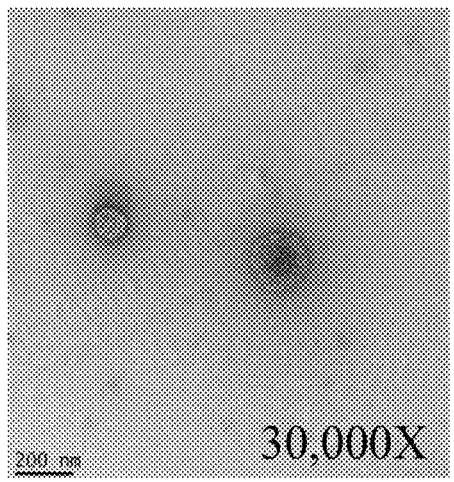
FIG. 9A and FIG. 9B show transmission electron microscopic (TEM) images of FePt@FTY720 NPs in accordance with an embodiment of the present disclosure.
Figure 9B:
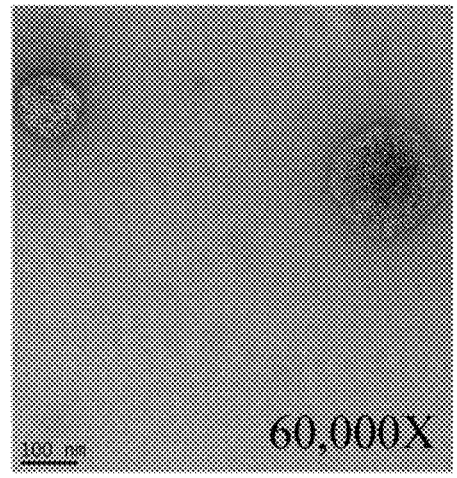
Figure 9C:
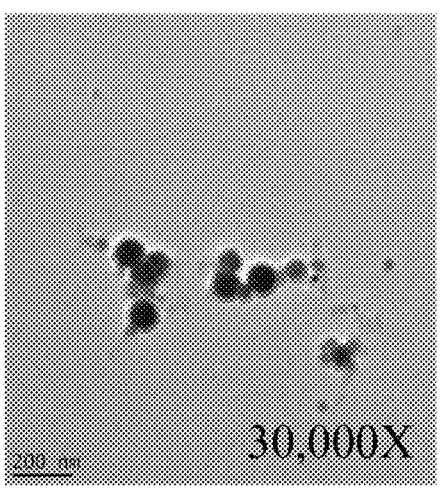
FIG. 9C and FIG. 9D show cryo-electron microscopic (cryo-EM) images of FePt@FTY720 NPs of the first exemplary embodiment in accordance with an embodiment of the present disclosure.
Figure 9D:
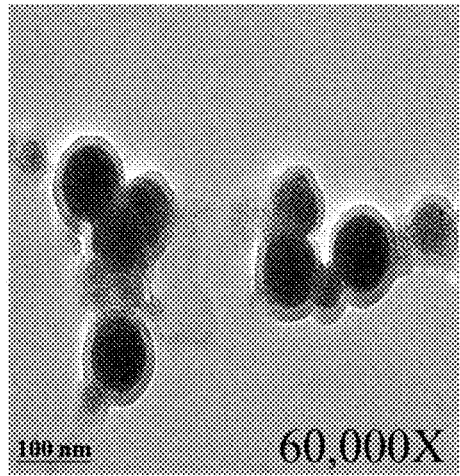
Figure 10A:
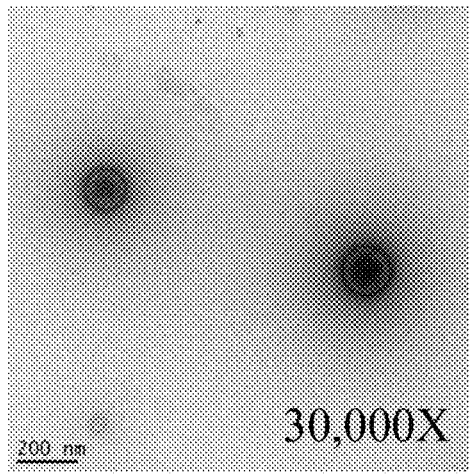
FIG. 10A and FIG. 10B show TEM images of FePt@FTY720-PVA NPs in accordance with an embodiment of the present disclosure.
Figure 10B:
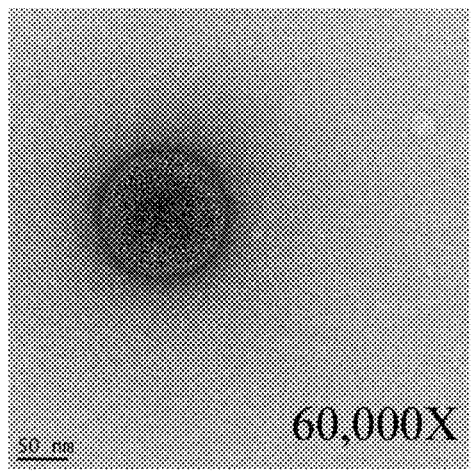
Figure 10C:
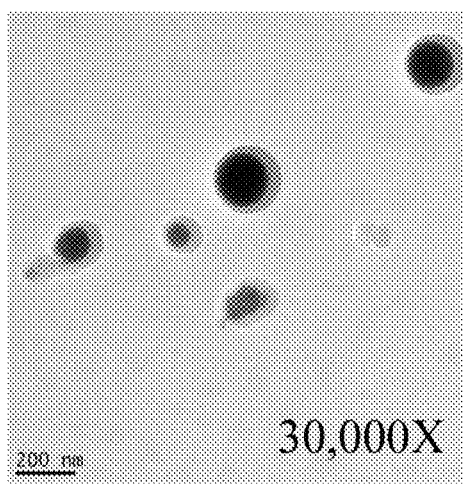
FIG. 10C and FIG. 10D show Cryo-EM images of FePt@FTY720-PVA NPs in accordance with an embodiment of the present disclosure.
Figure 10D:
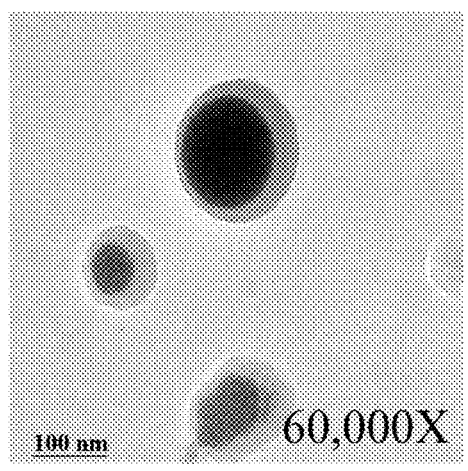

Referring to FIG. 8. In an example as illustrated in FIG. 8, the method for preparing FePt@FTY720 NPs or FePt@FTY720-PVA NPs by nanoprecipitation includes the steps of: dissolving 5 mg of FePt NPs having a particle diameter of 6 nm in 100 μL of dichloromethane (DCM) to obtain a first solution, and dissolving 3 mg of FTY720 in 900 μL of water to obtain a second solution; mixing the first and the second solutions by pipetting to obtain a homogenized mixture; injecting 9 mL of $H_2O$ or 1% PVA in $H_2O$ into the mixture and subjecting the mixture to ultrasound for 5 minutes; vacuuming the mixture for 15 min to evaporate the DCM; centrifuging the mixture to remove excess FTY720 and PVA to obtain a precipitate; and washing the precipitate twice by water to obtain FePt@FTY720 NPs and FePt@FTY720-PVA NPs.

In the example, the mass ratio of FePt NPs to FTY720 is in the range of 1:0.01 to 1:100. The weight percentage of PVA in the FePt@FTY720-PVA NPs is about 1%. Further, sudden decrease in solvent hydrophobicity during the vacuum evaporation step leads to aggregation of FTY720 and hydrophobic portions of the FePt NPs, thus loading the therapeutic agent FTY720 onto the metal nanoparticles.

Referring to FIG. 9A to FIG. 9D. Characterization of the FePt@FTY720 NPs prepared according the steps illustrated in FIG. 8 by transmission electron microscope (TEM) and cryo-electron microscope (Cryo-EM) revealed that an average diameter of the FePt @ FTY720 NPs falls substantially within a range of 84.4±12.3 nm.

Referring to FIG. 10A to FIG. 10D. Characterization of the FePt@FTY720-PVA NPs prepared according the steps illustrated in FIG. 8 by TEM and Cryo-EM revealed that an average diameter of the FePt@FTY720-PVA NPs falls substantially within a range of 71.7±23.6 nm.

Figure 11:
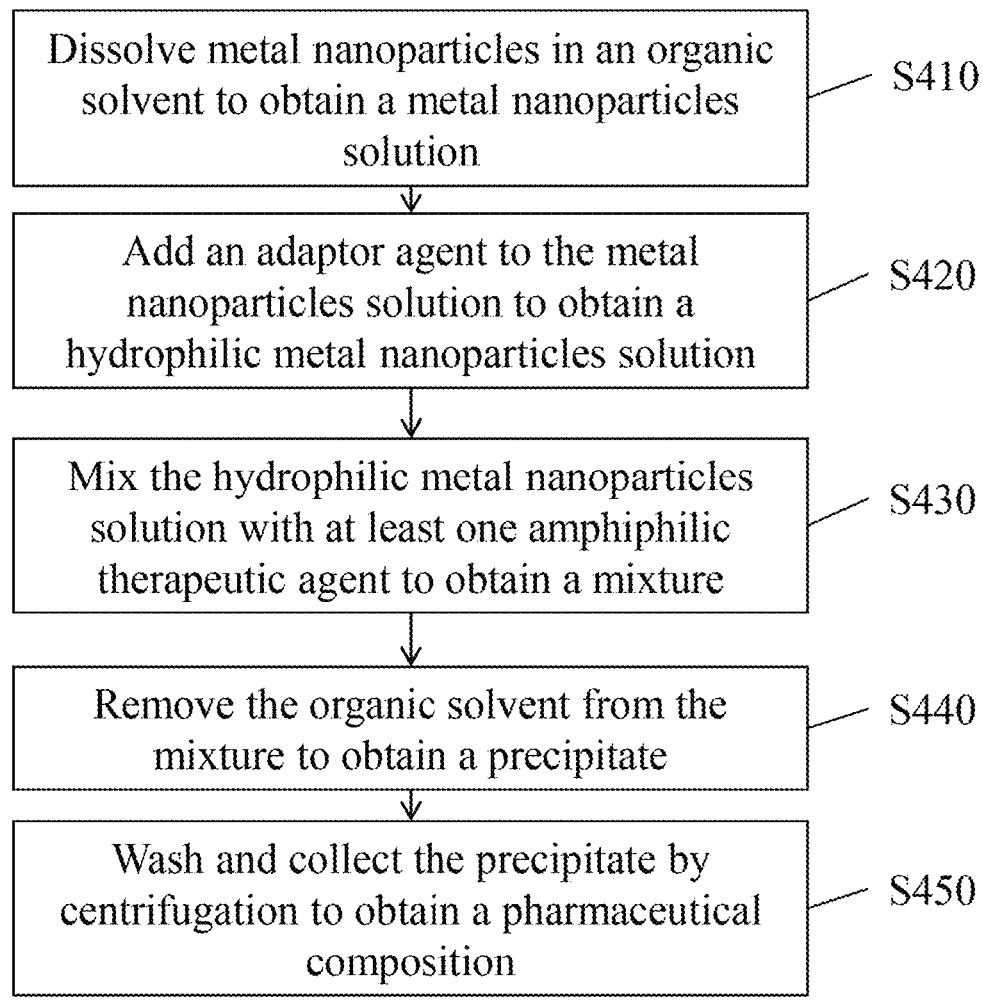
FIG. 11 is a flow diagram of a method for preparing FePt@PEG-FTY720 NPs in accordance with another embodiment of the present disclosure.

Referring to FIG. 11. According to an embodiment of the present disclosure, the method for preparing a pharmaceutical composition containing metal nanoparticles covered with a therapeutic agent and an adapter agent includes the steps of: (S410) dissolving metal nanoparticles in an organic solvent to obtain a metal nanoparticles solution; (S420) adding an adaptor agent to the metal nanoparticles solution to obtain a hydrophilic metal nanoparticles solution; (S430) mixing the hydrophilic metal nanoparticles solution with at least one amphiphilic therapeutic agent to obtain a mixture; (S440) removing the organic solvent from the mixture to obtain a precipitate; and (S450) washing the precipitate and collecting the precipitate by centrifugation to obtain the pharmaceutical composition.

In an example, by using FePt NPs having a particle diameter of 6 nm as the metal nanoparticles, FTY720 as the therapeutic agent (with the mass ratio of FePt NPs to FTY720 being 1:0.01 to 100) and PEG as the adaptor agent, the pharmaceutical composition of FePt@PEG-FTY720 NPs can be synthesized according to the steps exemplified in FIG. 11.

Figure 12:
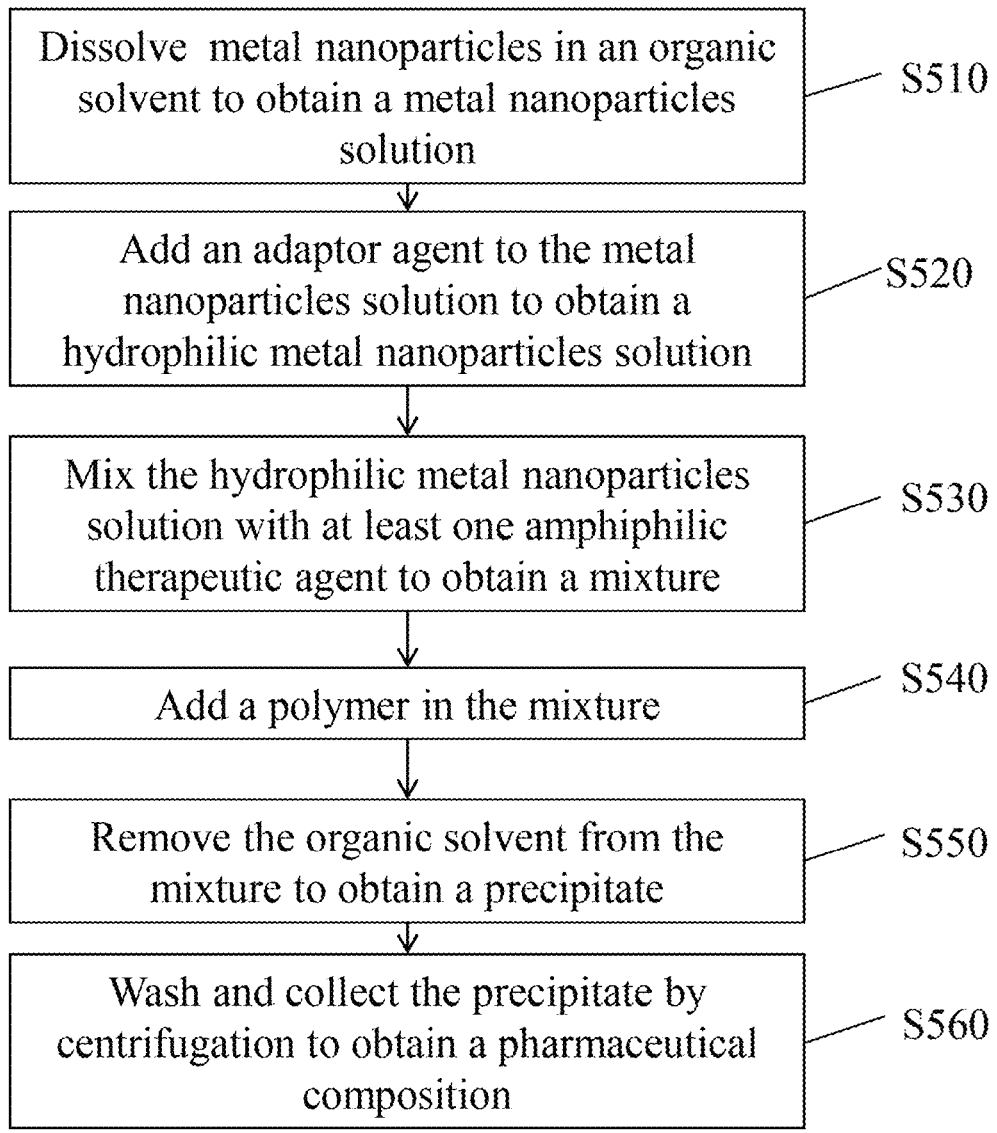
FIG. 12 is a flow diagram of a method for preparing FePt@PEG-FTY720-PVA NPs in accordance with another embodiment of the present disclosure.

Referring to FIG. 12. According to an embodiment of the present disclosure, the method for preparing a pharmaceutical composition containing metal nanoparticles covered with a therapeutic agent and an adapter agent and encapsulated by a polymer shell includes the steps of: (S510) dissolving metal nanoparticles in an organic solvent to obtain a metal nanoparticles solution; (S520) adding an adaptor agent to the metal nanoparticles solution to obtain a hydrophilic metal nanoparticles solution; (S530) mixing the hydrophilic metal nanoparticles solution with at least one amphiphilic therapeutic agent to obtain a mixture; (S540) adding a polymer in the mixture; (S550) removing the organic solvent from the mixture to obtain a precipitate; and (S560) washing the precipitate and collecting the precipitate by centrifugation to obtain the pharmaceutical composition.

In an example, by using FePt NPs having a particle diameter of 6 nm as the metal nanoparticles, FTY720 as the therapeutic agent (with the mass ratio of FePt NPs to FTY720 being 1:0.01 to 100), PEG as the adaptor agent and PVA as the polymer shell (with the weight percentage being 0.1%-10% or preferably 0.25%-5%), the pharmaceutical composition of FePt@PEG-FTY720-PVA NPs can be synthesized according to the steps exemplified in FIG. 12.

Figure 13:
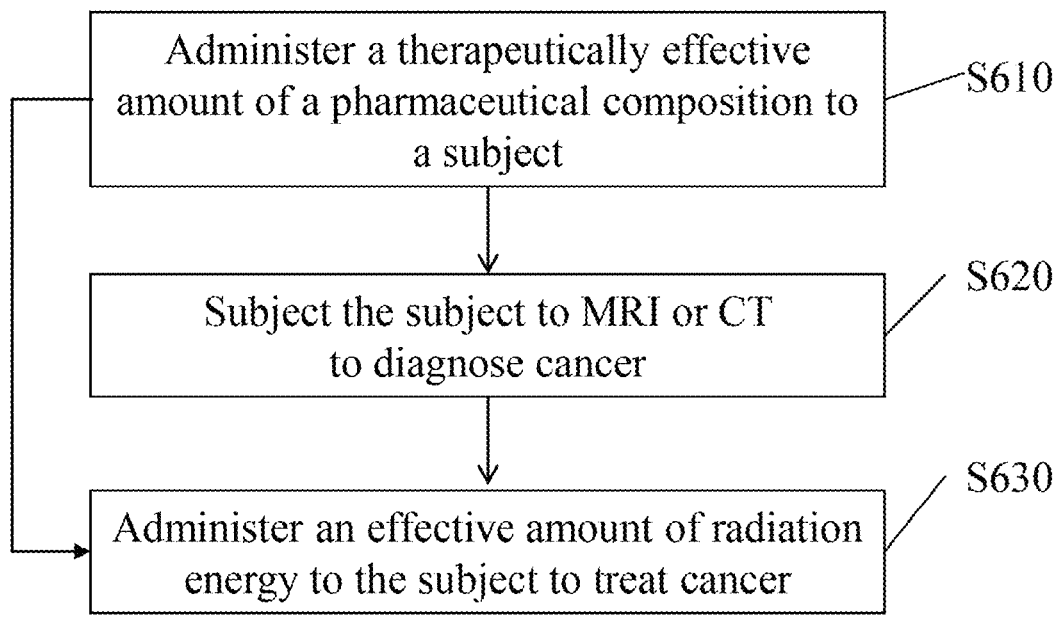
FIG. 13 shows a flow diagram of a method for delivering a therapeutic agent of the pharmaceutical composition to a subject in accordance with an embodiment of the present disclosure.

Referring to FIG. 13. According to an embodiment of the present disclosure, a method for using a pharmaceutical composition containing the metal nanoparticles and the therapeutic agent (e.g., FePt@FTY720 NPs or FePt@PEG-FTY720 NPs) includes the step of: (S610) administering a therapeutically effective amount of a pharmaceutical composition to a subject orally, intravenously, subcutaneously, or intramuscularly. Prior to step S610, the method may further include a step of configuring the pharmaceutical composition by, for example, combining the pharmaceutical composition with a pharmaceutically acceptable carrier.

In an embodiment, the method may further include a step of (S620) subjecting the subject to MRI or CT scanning to diagnose and locate cancer in the subject, or a step of (S630) administering an effective amount of radiation energy to the subject to treat cancer in the subject. In another embodiment, the method may further include the steps of S620 and S630, so that cancerous tissues in the subject is located and treated simultaneously.

Figure 14:
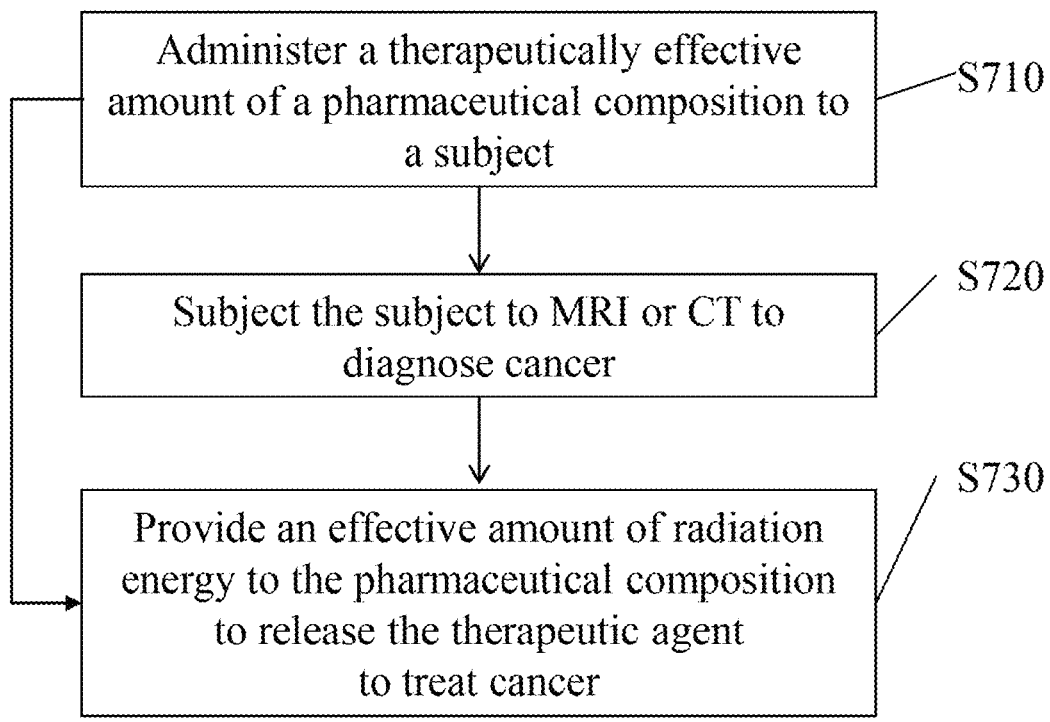
FIG. 14 shows a flow diagram of a method for treating cancer by using the pharmaceutical composition in accordance with an embodiment of the present disclosure.

Referring to FIG. 14. According to an embodiment of the present disclosure, a method for using a pharmaceutical composition containing the metal nanoparticles, the therapeutic agent, and the polymer shell (e.g., FePt@FTY720-PVA NPs or FePt@PEG-FTY720-PVA NPs) includes the step of: (S710) administering a therapeutically effective amount of a pharmaceutical composition to a subject orally, intravenously, subcutaneously, or intramuscularly. Prior to step S710, the method may further include a step of configuring the pharmaceutical composition by, for example, combining the pharmaceutical composition with a pharmaceutically acceptable carrier.

In an embodiment, the method may further include a step of (S720) subjecting the subject to MRI or CT scanning to diagnose and locate cancer in the subject. In another embodiment, as the pharmaceutical composition contains the polymer shell that enables controlled release of the therapeutic agent, the method may further include a step of (S730) providing an effective amount of radiation energy to the pharmaceutical composition to release the therapeutic agent to treat cancer in the subject. The effective amount of radiation energy provided to the pharmaceutical composition may also be sufficient to treat cancer in the subject, therefore allowing the cancer to be treated simultaneously by the therapeutic agent and radiation. In some embodiments, the method may further include the steps of S720 and S730, so that cancerous tissues in the subject is located and treated simultaneously.

Figure 15A:
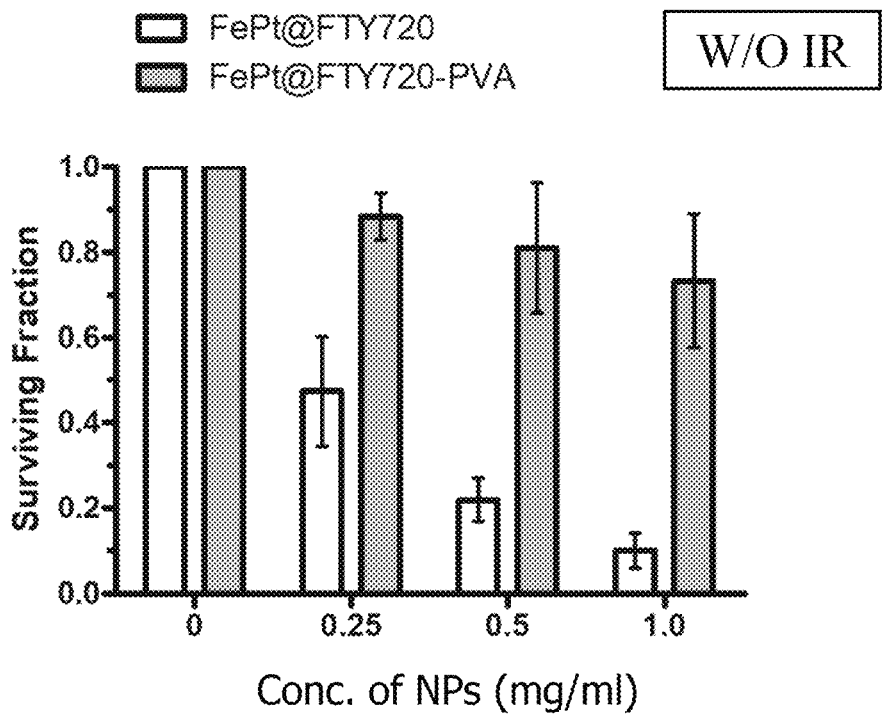
FIG. 15A graphically depicts assay analysis results of surviving fractions of tumor cells treated with different concentrations of pharmaceutical compositions, with or without polymer shell, in accordance with the embodiments of the present disclosure.
Figure 15B:
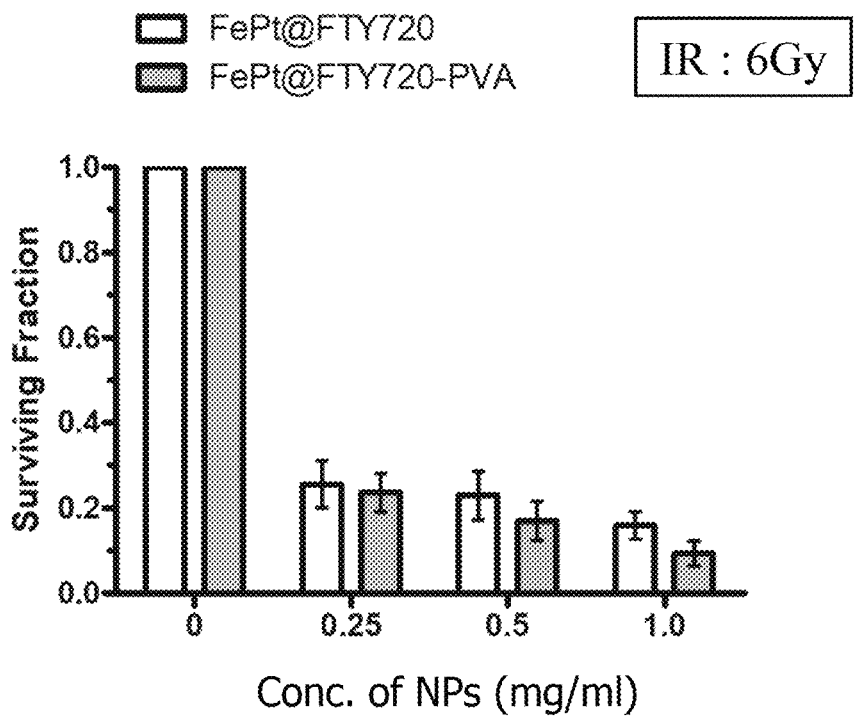
FIG. 15B graphically depicts assay analysis results of surviving fractions of tumor cells treated different concentrations of pharmaceutical compositions, with or without polymer shell, in conjunction with radiation therapy (RT) in accordance with the embodiments of the present disclosure.

Referring to FIG. 15A and FIG. 15B. Efficacy of the pharmaceutical compositions according to various embodiments of the present disclosure is examined. Specifically, survival of human lung cancer SR3A-13 cells administered with different dosage of two types of FePt pharmaceutical compositions, without or with administering radiation energy (denoted IR in figure), is analyzed. In the exemplary demonstration, FePt@FTY720 NPs and FePt@FTY720-PVA NPs at concentrations of 0, 0.25, 0.5 and 1.0 mg/ml were incubated with SR3A-13 cells in vitro for 25 hours. The treated SR3A-13 cancer cells were divided into two groups, one of which was further treated with 6 Gy of radiation. Thereafter, all of the SR3A-13 cancer cells are trypsined and re-cultured in 10-cm petri dishes at different cell densities (e.g., 500-10000 cells per dish) for 10-14 days. Colonies in the culture are counted to obtain surviving fractions of the cells, as shown in FIG. 15A and FIG. 15B.

As demonstrated in FIG. 15A and FIG. 15B, FePt@FTY720 NPs have shown to enhance the synergistic effect of nanoparticle-based cancer treatment. Specifically, radiation exposure significantly reduced survival of FePt@FTY720-treated SR3A-13 cells, roughly from 50% to 30% when treated with 0.25 mg/mL of FePt@FTY720 NPs. The result provides a clear evident of FePt@FTY720's ability to synergize with radiation therapy.

In addition, FePt@FTY720 NPs have shown to induce a dose-dependent decrease in surviving fraction of the SR3A-13 cells, in regardless of whether radiation energy is administered thereto. In contrast, FePt@FTY720-PVA NPs caused a dose-dependent decrease in SR3A-13 survival, especially significantly when radiation energy is administered; furthermore, exposing FePt@FTY720-PVA NPs to radiation induces a cytotoxicity to the SR3A-13 cancer cells substantially similar to that of FePt@FTY720 NPs. These results suggest that unirradiated PVA polymer shell blocks release of FTY720 from the pharmaceutical composition and that the PVA polymer shell allows a controllable release of FTY720 by radiation.

Figure 16:
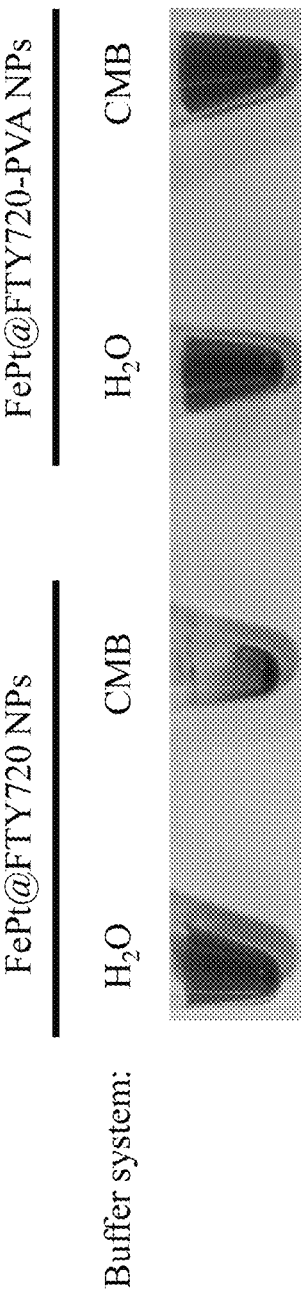
FIG. 16 shows the images of therapeutic agents of the pharmaceutical compositions in $H_2O$ or in a cytoplasm mimicking buffer system in accordance with embodiments of the present disclosure.

Referring to FIG. 16. Release of the therapeutic agent from the pharmaceutical composition in different buffer systems is analyzed. In the experiment shown in FIG. 16, the pharmaceutical compositions FePt@FTY720 NPs and FePt@FTY720-PVA NPs are tested in $H_2O$ and in cytoplasm mimicking buffer (CMB). To mimic the physiological conditions of tumor tissues, the CMB contained KCl (120 mM), $CaCl_2$) (0.15 mM), $K_2HPO_4/KH_2PO_4$ (10 mM), HEPES (25 mM), EGTA (2 mM), $MgCl_2$ (5 mM), ATP (2 mM), and glutathione (5 mM), and had a pH of about 7.6. The pharmaceutical compositions were let stand at room temperature for 24 hours, and observed by naked eyes for aggregation of FePt nanoparticles.

As demonstrated in FIG. 16, no precipitation was observed when FePt@FTY720 NPs and FePt@FTY720-PVA NPs are in $H_2O$, indicating that the FTY720 was not released in $H_2O$. In contrast, precipitate of metal nanoparticles was formed when FePt@FTY720 NPs are kept in CMB, suggesting that FTY720 is released from the FePt@FTY720 NPs. Furthermore, no precipitation was observed when FePt@FTY720-PVA NPs are kept in CMB, demonstrating that unirradiated PVA polymer shell effectively blocks release of FTY720 from FePt@FTY720-PVA NPs.

The pharmaceutical compositions according to various embodiments of the present disclosure includes metal nanoparticles (e.g., FePt NPs) and therapeutic agent(s) (e.g., FTY720), and have demonstrated to allow synchronism between diagnosis and treatment of cancer. The pharmaceutical compositions can also act as contrast agents for CT or MRI scanning, enhancers for enhancing therapeutic effect of radiation therapy by generating free radicals to destroy cancerous cells, and/or sensitizers for enhancing sensibility of cancerous cells to radiation or chemotherapies. The pharmaceutical composition containing FTY720 covered FePt NPs can also significantly increase radiation-sensitivity of cancer cells, and thereby improving therapeutic efficacy of cancer radiation therapy.

The pharmaceutical compositions according to other embodiments of the present disclosure include metal nanoparticles (e.g., FePt NPs), therapeutic agent(s) (e.g., FTY720) and polymer shells encapsulating the pharmaceutical compositions. The polymer shell significantly increases stability of the pharmaceutical compositions. As the metal nanoparticles can accumulate in tumor tissues, the polymer shell depolymerizes to release the therapeutic agent to the tumor tissues when radiation is applied to the pharmaceutical compositions. Therefore, the polymer shell can avoid adverse side effects caused by non-specific release of the therapeutic agent to normal tissues.

The embodiments illustrated and described above are only examples. Many details are often found in the art such as the other features of a pharmaceutical composition, and methods for preparing and using the pharmaceutical composition. Therefore, many such details are neither illustrated nor described. Even though numerous characteristics and advantages of the present technology have been set forth in the foregoing description, together with details of the structure and function of the present disclosure, the disclosure is illustrative only, and changes may be made in the detail, especially in matters of shape, size, and arrangement of the parts within the principles of the present disclosure, up to and including the full extent established by the broad general meaning of the terms used in the claims. It will therefore be appreciated that the embodiments described above may be modified within the scope of the claims.

What is claimed is:

1. A pharmaceutical composition, comprising:
    a plurality of nanoparticles, each of the nanoparticles comprising:
        an iron-platinum (FePt) core; and
        a hydrophobic stabilizing agent coated on a surface of the FePt core; and
    at least one therapeutic agent that consists of an amphiphilic compound directly attached to the hydrophobic stabilizing agent,
    wherein the therapeutic agent includes at least one hydrophobic chain that interacts directly with the hydrophobic stabilizing agent;
    wherein the at least one therapeutic agent is selected from a group consisting of 2-amino-2-[2-(4-octylphenyl) ethyl]-1,3-propanediol (FTY720), derivatives of FTY720, 2-amino-N-(3-octylphenyl)-3-(phosphonooxy)-propanamaide (VPC 23019), derivatives of VPC 23019, [(3R)-3-amino-4-[(3-hexylphenyl) amino]-4-oxobutyl]-phosphonic acid (W146), derivatives of W146, and a combination thereof.

2. The pharmaceutical composition of claim 1, wherein an average diameter of the nanoparticles falls substantially within a range of 3 nanometers (nm) to 13 nm.

3. The pharmaceutical composition of claim 1, wherein the hydrophobic stabilizing agent is oleic acid.

4. The pharmaceutical composition of claim 1, wherein the at least one therapeutic agent comprises an anti-cancer drug, an anti-inflammatory agent, or a combination thereof.

5. The pharmaceutical composition of claim 1, wherein a mass ratio of the nanoparticles to the at least one therapeutic agent falls substantially within a range of 1:0.01 to 1:100.

6. The pharmaceutical composition of claim 1, further comprising a polymer shell encapsulating the nanoparticles and the therapeutic agent.

7. The pharmaceutical composition of claim 6, wherein the polymer shell enables controlled release of the therapeutic agent.

8. The pharmaceutical composition of claim 6, wherein the polymer shell comprises polyvinyl alcohol (PVA), poly (lactic-co-glycolic acid) (PLGA), polyethylene glycol (PEG), D-α-tocopherol polyethylene glycol 1000 succinate (TPGS), or a combination thereof.

9. The pharmaceutical composition of claim 6, wherein a weight percentage of the polymer shell in the pharmaceutical composition falls within a range of 0.1% to 10%.

10. The pharmaceutical composition of claim 6, further comprising an adaptor agent linking the therapeutic agent to the hydrophobic stabilizing agent of the nanoparticles.

11. The pharmaceutical composition of claim 1, further comprising an adaptor agent linking the therapeutic agent to the hydrophobic stabilizing agent of the nanoparticles.

12. The pharmaceutical composition of claim 1, being bifunctional and used for diagnosing and treating cancer.

13. The pharmaceutical composition of claim 12, wherein the cancer comprises lung carcinoma or breast cancer.

14. A method for using a pharmaceutical composition, comprising:
    receiving the pharmaceutical composition comprising a plurality of nanoparticles and at least one therapeutic agent, wherein each of the nanoparticles comprises
        an FePt core and a hydrophobic stabilizing agent coated on a surface of the FePt core,
            wherein the at least one therapeutic agent consists of an amphiphilic compound directly attached to the hydrophobic stabilizing agent, wherein the therapeutic agent includes at least one hydrophobic chain that interacts directly with the hydrophobic stabilizing agent wherein the at least one therapeutic agent is selected from a group consisting of 2-amino-2-[2-(4-octylphenyl)ethyl]-1,3-propanediol (FTY720), derivatives of FTY720, 2-amino-N-(3-octylphenyl)-3-(phosphonooxy)-propanamaide (VPC 23019), derivatives of VPC 23019, [(3R)-3-amino-4-[(3-hexylphenyl)amino]-4-oxobutyl]-phosphonic acid (W146), derivatives of W146, and a combination thereof; and administering a therapeutically effective amount of the pharmaceutical composition to a subject.

15. The method of claim 14, further comprising:
administering an effective amount of radiation energy to the subject, wherein the effective amount of radiation energy is sufficient to treat cancer in the subject.

16. The method of claim 14, further comprising:
subjecting the subject to magnetic resonance imaging or computed tomography scanning to diagnose cancer in the subject.

17. The method of claim 14, further comprising:
subjecting the subject to magnetic resonance imaging or computed tomography scanning to diagnose cancer in the subject; and
administering an effective amount of radiation energy to the subject, wherein the effective amount of radiation energy is sufficient to treat cancer in the subject.

18. A method for using a pharmaceutical composition, the method comprising:
receiving a pharmaceutical composition that comprises
a plurality of nanoparticles,
at least one therapeutic agent, and
a polymer shell,
wherein each of the nanoparticles comprising
an FePt core, and
a hydrophobic stabilizing agent coated on a surface of the FePt core,
wherein the at least one therapeutic agent consists of an amphiphilic compound directly attached to the hydrophobic stabilizing agent, and the polymer shell encapsulating the nanoparticles and the therapeutic agent, wherein the therapeutic agent includes at least one hydrophobic chain that interacts directly with the hydrophobic stabilizing agent wherein the at least one therapeutic agent is selected from a group consisting of 2-amino-2-[2-(4-octylphenyl)ethyl]-1,3-propanediol (FTY720), derivatives of FTY720, 2-amino-N-(3-octylphenyl)-3-(phosphonooxy)-propanamaide (VPC 23019), derivatives of VPC 23019, [(3R)-3-amino-4-[(3-hexylphenyl)amino]-4-oxobutyl]-phosphonic acid (W146), derivatives of W146, and a combination thereof; and administering a therapeutically effective amount of the pharmaceutical composition to a subject.

19. The method of claim 18, further comprising:
administering an effective amount of radiation energy to the subject, wherein the effective amount of radiation energy is sufficient to treat cancer in the subject.

20. The method of claim 18, further comprising:
subjecting the subject to magnetic resonance imaging or computed tomography scanning to diagnose cancer in the subject.

21. The method of claim 18, further comprising:
subjecting the subject to magnetic resonance imaging or computed tomography scanning to diagnose cancer in the subject; and
administering an effective amount of radiation energy to the cancer cells in the subject.

22. The method of claim 18, further comprising:
providing an effective amount of radiation energy to the pharmaceutical composition to release the therapeutic agent into the subject.

23. The method of claim 22, wherein the effective amount of radiation energy is sufficient to treat cancer in the subject.

24. The method of claim 18, further comprising:
subjecting the subject to magnetic resonance imaging or computed tomography scanning to diagnose cancer in the subject; and
providing an effective amount of radiation energy to the pharmaceutical composition to release the therapeutic agent into the subject.

25. The method of claim 24, wherein the effective amount of radiation energy is sufficient to treat cancer in the subject.

* * * * *